(12) United States Patent
Todd et al.

(10) Patent No.: US 6,245,505 B1
(45) Date of Patent: Jun. 12, 2001

(54) SELECTIVE LIGATION AND AMPLIFICATION METHOD

(75) Inventors: Alison Velyain Todd, Hondi Beach; Caroline Jane Fuery, Balga, both of (AU)

(73) Assignee: Johnson & Johnson Research Pty. Limited, St. Leonards (AU)

( * ) Notice: Subject to any disclaimer, the term of this patent is extended or adjusted under 35 U.S.C. 154(b) by 0 days.

(21) Appl. No.: 09/367,825

(22) PCT Filed: Feb. 23, 1998

(86) PCT No.: PCT/AU98/00114

§ 371 Date: Dec. 17, 1999

§ 102(e) Date: Dec. 17, 1999

(87) PCT Pub. No.: WO98/37230

PCT Pub. Date: Aug. 27, 1998

(30) Foreign Application Priority Data

Feb. 21, 1997 (AU) .................................................. PO 5248

(51) Int. Cl.[7] ...................................................... C12Q 1/68
(52) U.S. Cl. .................................. 435/5; 435/5; 435/91.1; 435/91.2; 435/91.5; 435/94; 435/183; 536/24.3; 536/24.31; 536/24.33
(58) Field of Search ..................................... 435/6, 5, 91.1, 435/91.2, 91.5, 94, 183; 536/24.3, 24.31, 24.33

(56) References Cited

U.S. PATENT DOCUMENTS 5,593,840 * 1/1997 Bhatnagar et al. ...................... 435/6

FOREIGN PATENT DOCUMENTS

| WO 94/17210 | 8/1994 | (WO) . |
| WO 94/29481 | 12/1994 | (WO) . |
| WO 96/39537 | 12/1996 | (WO) . |
| WO 96/40992 | 12/1996 | (WO) . |
| WO 96/40995 | 12/1996 | (WO) . |

OTHER PUBLICATIONS

Dilsiz, Nihat et al., "A High–Yield Modification of Mutation by Overlap Extension Using Three Primers.", Analytical Biochemistry, vol. 222, No. 2, pp. 510–511 (1991).

Lehman, Teresa et al., "Detection of K–ras Oncogene Mutations by Polymerase Chain Reaction–Based Ligase Chain Reaction.", Analytical Biochemistry, vol. 239, No. 2, pp. 153–159 (1996).

Weisberg, Edward et al., "Simultaneous Mutagenesis of Multiple Sites:Application of the Ligase Chain Reaction Using PCR Products Instead of Oligonucleotides.", Biotechniques, vol. 15, No. 1, pp. 68–76 (1993).

Baldrich, Marcus et al., "Rapid and efficient site–specific mutagenesis.", Protein Engineering, vol. 3, No. 6, pp. 563 (1990).

(List continued on next page.)

Primary Examiner—W. Gary Jones
Assistant Examiner—Janell E. Taylor
(74) Attorney, Agent, or Firm—Browdy and Neimark (57) ABSTRACT

The present invention provides a method for amplifying a specific target nucleic acid sequence. The method comprises (1) forming a reaction mixture comprising: (i) the target sequence; (ii) primers comprising a first primer at least a portion of which at the 3' end thereof is substantially complementary to a first segment at a first end of the target sequence, a second primer at least a portion of which at the 5' end thereof is substantially complementary to a second segment at a second end of the target sequence, the 5' end of the second primer being adjacent the 3' end of the first primer, and a third primer, the third primer being substantially complementary to a segment of the second primer at the 3' end thereof; (iii) at least four different nucleotide bases; (iv) thermostable polymerase and thermostable ligase; and (2) thermocycling the reaction mixture.

6 Claims, 6 Drawing Sheets and

OTHER PUBLICATIONS

Michael, Scott F., "Thermostable Ligase–Mediated Incorporation of Mutagenic Oligonucleotides During PCR amplification.", Methods in Molecular Biology, vol. 67, pp. 189–195 (1997).

Shayiq, Rass M. et al., "Multiple in vitro Site–Directed Mutagenesis Using Asymmetric Polymerase Chain Reaction."Analytical Biochemistry, vol. 221, No. 1, pp. 206–208 (1994).

* cited by examiner

Note: the 5'GP has the same sequence as the RS at the 5' end of the 5'LP

Figure 6

SELECTIVE LIGATION AND AMPLIFICATION METHOD

CROSS REFERENCE TO RELATED APPLICATION

The present application is the national stage under 35 U.S.C. 371 of PCT/AU98/00114, filed Feb. 21, 1997.

FIELD OF THE INVENTION

The present invention relates to methods for in vitro amplification of specific nucleic acid target sequences. In particular the invention relates to methods which initially depend on concurrent DNA polymerase and ligase activity to mediate amplification of nucleic acid targets. The method can be used to selectively amplify nucleic acid sequences which contain sequence variations such as point mutations, deletions and insertions.

BACKGROUND OF THE INVENTION

A variety of inherited and acquired diseases are associated with genetic variations such as point mutations, deletions and insertions. Some of these variants are directly associated with the presence of disease, while others correlate with disease risk and/or prognosis. There are more than 500 human genetic diseases which result from mutations in single genes. These include cystic fibrosis, muscular dystrophy, α1-antitrypsin deficiency, phenylketonuria, sickle cell anaemia or trait, and various other haemoglobinopathies. Furthermore, individuals with increased susceptibility to several common polygenic conditions, such as atherosclerotic heart disease, have been shown to have an association with the inheritance of a particular DNA sequence polymorphism. Cancer is thought to develop due the accumulation of genetic lesions in genes involved in cellular proliferation or differentiation. The ras proto-oncogenes, K-ras, N-ras, and H-ras, and the p53 tumor suppressor gene are examples of genes which are frequently mutated in human cancers. Specific mutations in these genes result in an increase in transforming potential. Genetic analysis is likely to become routine in the clinic for assessing disease risk, diagnosis of disease, predicting a patient's prognosis or response to therapy, and for monitoring a patient's progress. The introduction of such genetic tests depends on the development of simple, inexpensive, and rapid assays for genetic variations.

Due to increasing interest in the development of such tests a number references have been published in this area, these include, Abravaya, K., Carrino, J. J., Muldoon, S. and Lee, H. H. (1995) Detection of point mutations with a modified ligase chain reaction (Gap-LCR). Nucleic Acids Research 23, 675–682; Barany, F. (1991) Genetic disease detection and DNA amplification using cloned thermostable ligase. Proc. Natl. Acad. Sci. 88, 189–193; Belgrader, P., Marino, M. M., Lubin, M. and Barany, F. (1996) A multiplex PCR-Ligase detection reaction assay for human identity testing. Genome Science and Technology 1, 77–87; and Eggerding, F. A. (1995) A one-step coupled amplification and oligonucleotide ligation procedure for multiplex genetic typing. PCR Methods and Applications 4, 337–345.

In U.S. Pat. No. 5,593,840 there is disclosed a method of detecting a particular nucleic acid sequence. The method disclosed in this patent is said to be based on the discovery that certain aspects of polymerase chain reaction (PCR) and ligase chain reaction (LCR) can be used in combination to detect and amplify a target nucleic acid sequence. This method involves the use of three primers, with the third primer being complementary to at least a portion of the 5' end of the first primer. It is an essential feature of this method that the position of the third primer complementary to the base at the 5' end of the first primer contains a modification such as to substantially avoid strand displacement by polymerase.

Further information regarding PCR and LCR can be found in U.S. Pat. Nos. 4,683,202, 4,683,195, 4,800,159, 4,965,188, 5,176,995, EP 0 320 308 and EP 0 439 182 and the disclosure of these references is included herein by reference.

SUMMARY OF THE INVENTION

The present inventors have developed a sensitive and selective procedure for amplification of specific target nucleic acid sequences. The method involves both LCR and PCR. As the method involves Selective Ligation and PCR it has been termed "SLAP".

Accordingly, in a first aspect the present invention consists in a ethod for amplifying a specific target nucleic acid sequence, the method comprising:
(1) forming a reaction mixture comprising:
   (i) the target sequence;
   (ii) primers comprising a first primer at least a portion of which at the 3' end thereof is substantially complementary to a first segment at a first end of the target sequence, a second primer at least a portion of which at the 5' end thereof is substantially complementary to a second segment at a second end of the target sequence, the 5' end of the second primer being adjacent the 3 end of the first primer. and a third primer, the third primer being substantially complementary to a segment of the second primer at the 3' end thereof;
   (iii) at least four different nucleotide bases;
   (iv) thermostable polymerase and thermostable ligase; and
(2) thermocycling the reaction mixture.

In a second aspect the present invention consists in a method for detecting a specific target nucleic acid sequence in a sample comprising nucleic acid, the method comprising:
(1) forming a reaction mixture comprising:
   (i) a sample of nucleic acid suspected to include the target sequence;
   (ii) primers comprising a first primer at least a portion of which at the 3' end thereof is substantially complementary to a first segment at a first end of the target sequence, a second primer at least a portion of which at the 5' end thereof is substantially complementary to a second segment at a second end of the target sequence, the 5' end of the second primer being adjacent the 3' end of the first primer, and a third primer, the third primer being substantially complementary to a segment of the second primer at the 3' end thereof;
   (iii) at least four different nucleotide bases;
   (iv) thermostable polymerase and thermostable ligase;
(2) thermocycling the reaction mixture; and
   (3) detecting the presence or absence of an amplification product indicative of the presence of the specific target nucleic acid sequence.

In a preferred embodiment of the present invention the method further comprises. following the thermocycling of the reaction mixture the steps of substantially inactivating the thermostable polymerase and a subsequent second thermocycling of the reaction mixture.

In a preferred embodiment of the present invention the segment of the second primer to which the third primer is substantially complementary is a random sequence.

In a further preferred embodiment the reaction mixture includes a fourth primer which has the same sequence as a segment of the first primer at the 5' end thereof.

The methods of the present invention can be used to simply amplify selected sequences. The method can also be used to determine the presence of particular sequences including for example to determine the presence of a mutation, allele, presence of a particular organism or virus. The target sequence can accordingly be from any source, including for example human and nonhuman animals, bacteria, yeast, fungi and viruses.

As used herein the term "random sequence" is intend to mean a sequence which is unrelated to the target sequence.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

DETAILED DESCRIPTION OF THE INVENTION (Strategy for Selective Ligation and PCR (SLAP))

In order that the nature of the present invention may be more clearly understood a preferred form thereof will now be described with reference to the following non-limiting general description of the operation of the method of the present invention and the following Example.

Figure Legends

Figure 1:
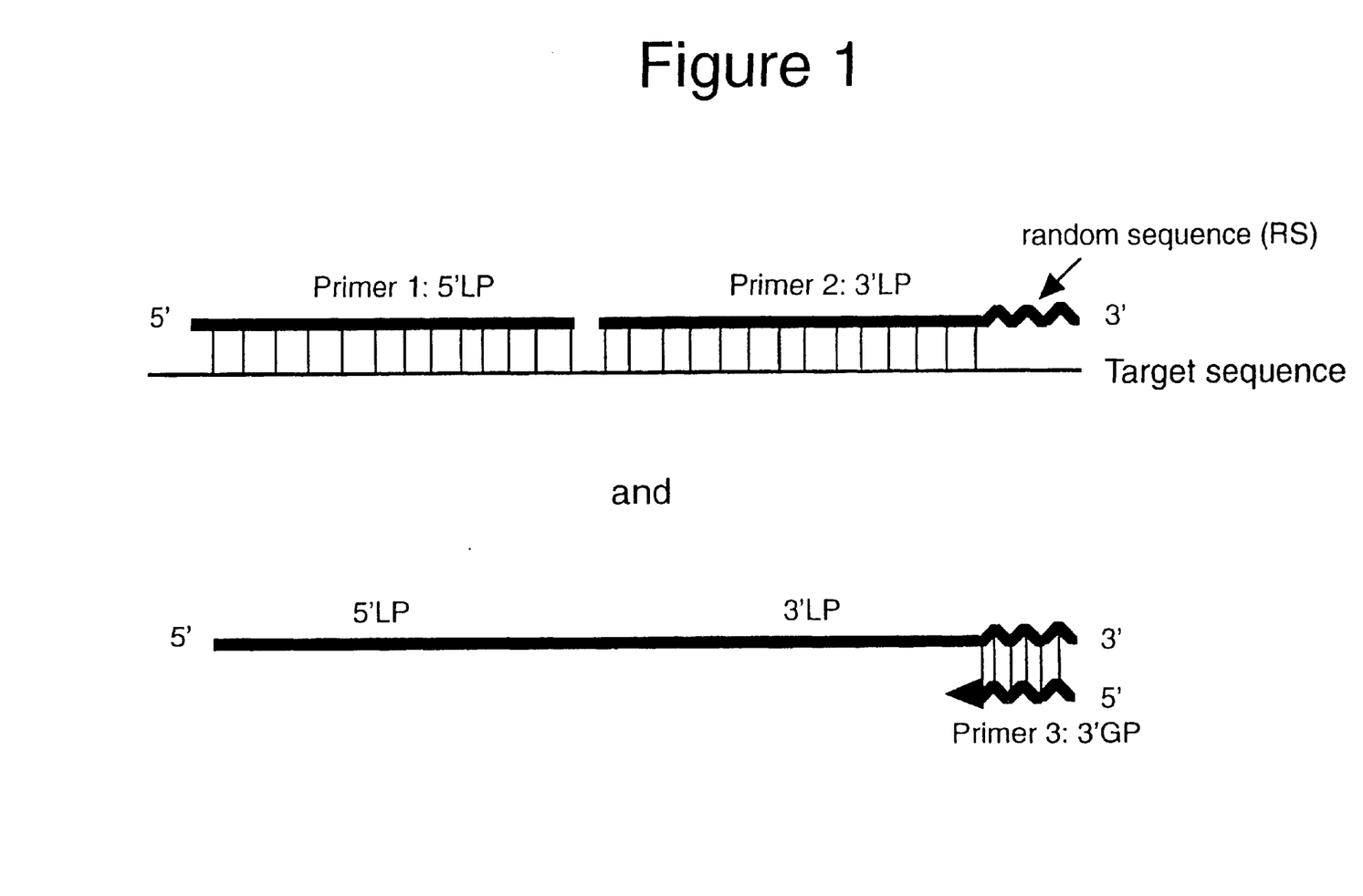
FIG. 1 SLAP—Arrangement of primers in a 3 primer system.

The general strategy for amplification by SLAP is described below and illustrated in FIGS. 1–3.

The method can be performed with three primers. These are the 5' ligation primer (5'LP), the 3' ligation primer (3'LP) and a generic primer (GP) (FIG. 1). The LPs are either fully, or partially, complementary to the target sequence. The GP is complementary to random sequence (RS) located at the terminus of the LP's e.g. at the 3' terminus of the 3'LP. The 3' terminus of the 5'LP and the 5' terminus of 3'LP can hybridize to regions which are either immediately adjacent on the target sequence (FIG. 2A (ii) and B) or they can hybridize to two regions separated by a gap of one or more nucleotides (FIG. 2A (i)). The inclusion of variant bases in the LPs allows the method to be used for screening single point mutations (base substitutions). The variant bases are either matched to the wild type sequence or to a specific base substitution. The variant base can be located either at or near the 3' terminus of the 5'LP (FIG. 2A) or at the 5' terminus of the 3'LP (FIG. 2B).

Figure 2:
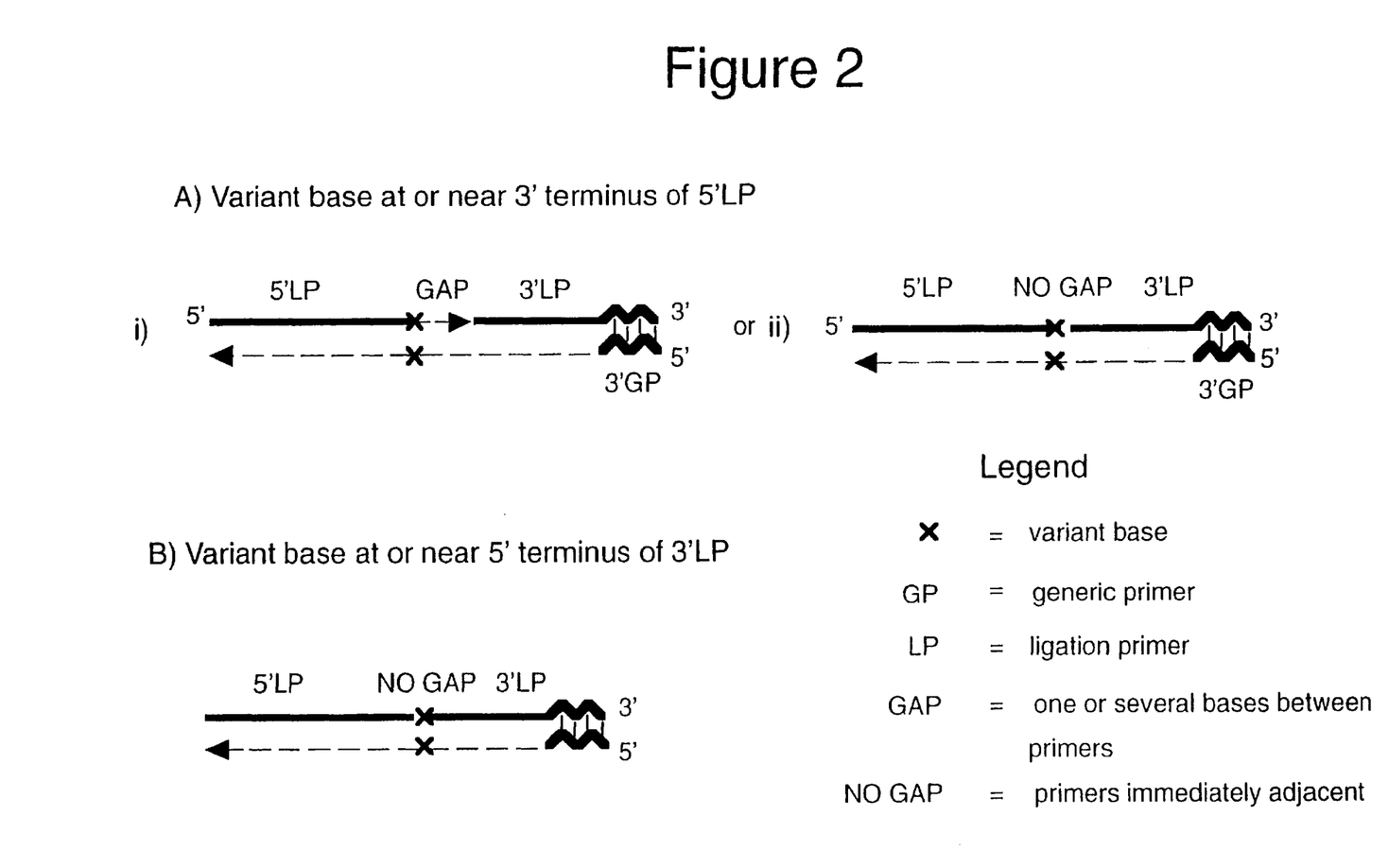
FIG. 2 Location of the variant base in primers for SLAP.

Additional Features of LPs Can Include (i) The 5'LP has a 3' hydroxyl group so that it can be either ligated with the 3'LP (FIG. 2 A (ii) and B) or be extended by DNA polymerase prior to ligation to the 3'LP (FIG. 2A (i)). The 5' terminus of the 5'LP can be modified (eg hydroxylated) so that it can not ligate to other fragments at this terminus.

(ii) The 3'LP is phosphorylated at the 5' terminus to allow ligation to the 5'LP or to extension products of the 5'LP. The 3' terminus of the 3'LP can be modified (eg phosphorylated) to prevent extension by DNA polymerase and/or ligation to other fragments at this terminus.

Figure 3:
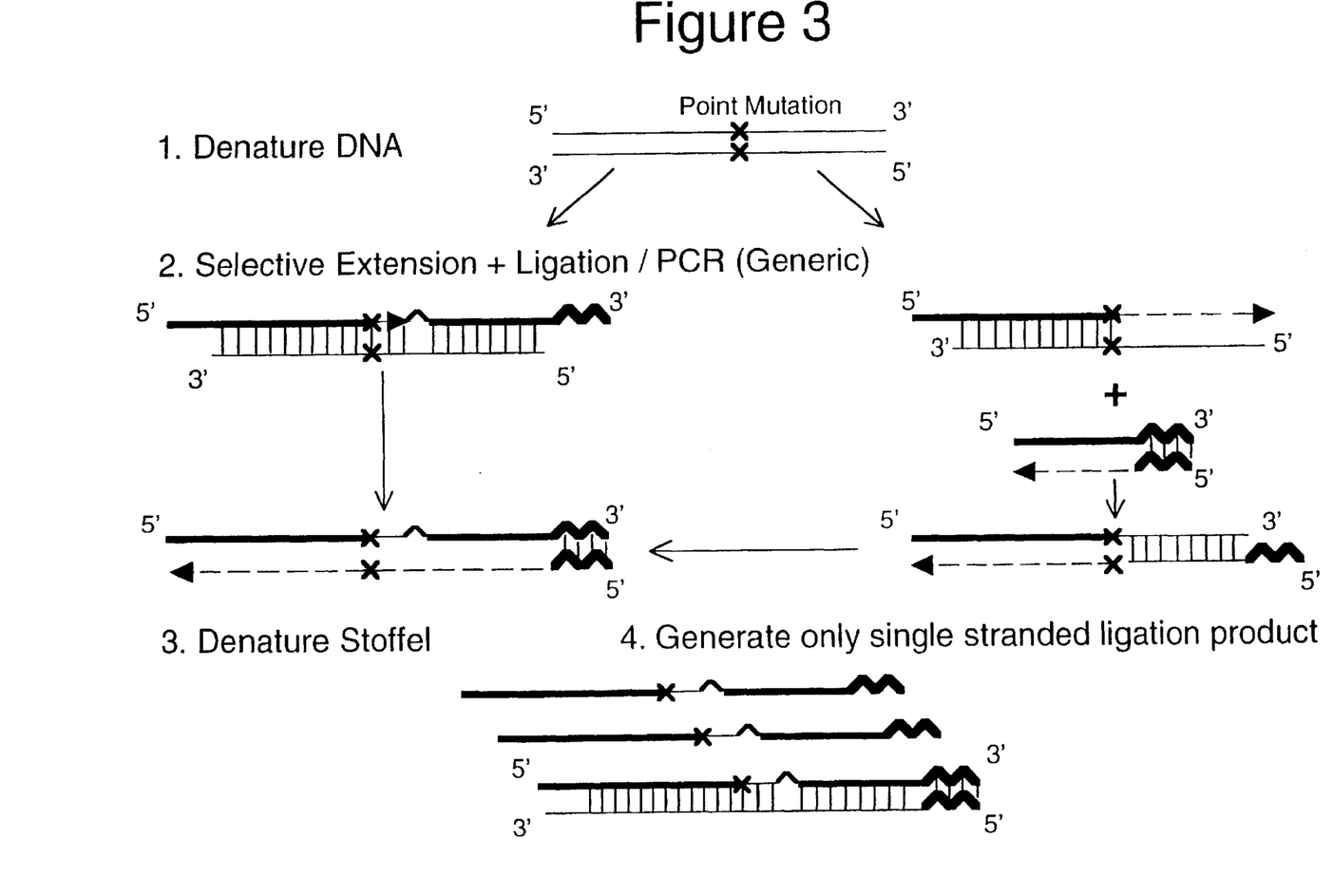
FIG. 3 SLAP

The steps required for amplification by SLAP are illustrated in FIG. 3. All steps in the reaction are performed in a single tube and all reagents are present at the beginning of the reaction. The individual steps are mediated in part by varying the temperature of the reaction. The strategy involves an initial phase which utilizes concurrent selective ligation and selective PCR. This stage of the reaction requires the activity of both thermostable ligase and DNA polymerase. PCR is mediated by one sequence specific primer (5'LP) and one generic primer (GP). After the initial phase the reaction is heated to denature the DNA polymerase. Since the ligase is in excess compared to the DNA polymerase, significant ligase activity is retained and during the second phase of the reaction single stranded product is generated by ligation. The amount of reagents required for PCR, eg DNA polymerase, generic primers and dNTPs, can be present in limiting amounts to favour ligation over PCR in the second phase of the reaction. The individual steps involved in the reaction are described in greater detail below. The example describes the steps (FIG. 3) for a primer arrangement similar to that as illustrated in FIG. 2A (i).

Step 1: DNA Denaturation.

Genomic DNA (target template) is rendered single stranded by heating at a high temperature.

Step 2: Selective Extension (filling GAP)/Selective Ligation and Generic PCR

The 5'LP and the 3'LP anneal to the denatured DNA template. Provided the 5'LP is fully matched at the 3' terminus, it is extended by DNA polymerase (eg. DNA polymerase, Stoffel fragment) and then ligated to the 3'LP by a thermostable ligase.

During this initial phase there is concurrent ligation and polymerisation. One strand is produced by either a) Extension of the 5'LP by DNA polymerase to fill in the gap, followed by ligation to the 3'LP (FIG. 3a); or b) Extension of the 5'LP by DNA polymerase using the target as template (FIG. 3b).

The complementary strand is produced by extension with the 3'GP. The template can be either a) the product formed by extension of the 5'LP by polymerase followed by ligation to the 3'LP or b) the product formed by extension of the 5'LP by polymerase using the target as template. The product formed by extension of the 3'LP as it copies the 3'LP (FIG. 3c) can be further extended by polymerase in subsequent rounds of PCR (FIG. 3d). Since PCR is generic it would be expected that all products would amplify with approximately equivalent efficiency.

Step 3: Denaturation of the DNA Polymerase

The temperature is elevated to denature the DNA polymerase. Since ligase is initially in excess there is still significant ligase activity. The remaining PCR reagents, eg residual active DNA polymerase, generic primers and dNTPs, allow gap filling but are insufficient to maintain efficient amplification by PCR.

Step 4: Generation of Single Stranded Product by Ligation

The major product formed in the final stage is single stranded product which results from the ligation of the (extended) 5'LP to the 3'LP.

Detection

Detection of single stranded ligation product can be mediated by several strategies including capture with oligonucleotides. One strategy for detection of the products includes labelling the 3'LP and capturing the product with oligonucleotides which hybridize to a segment that is 5' of the ligation site.

Capture oligonucleotides can be either target gene specific (complementary to target sequences) or generic (complementary to random sequence on a LP).

Figure 4:
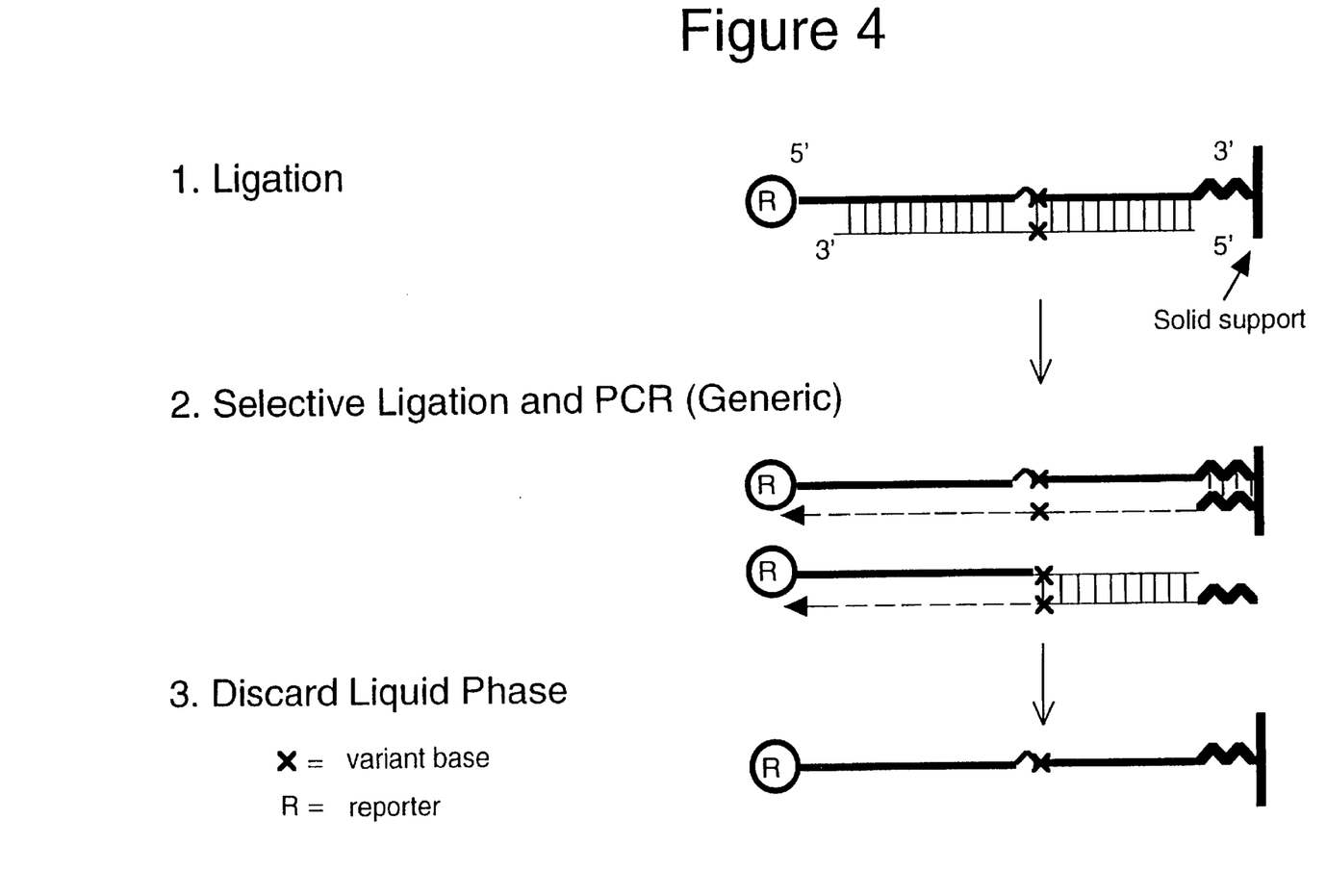
FIG. 4 Selective ligation and PCR

Alternate Strategies for SLAP (1) An alternative Strategy for SLAP is Illustrated in FIG. 4.

Steps 1 and 2 (denaturation plus selective ligation and PCR) are performed as described above. In this alternative strategy the 3'LP is attached to a solid phase. The 5'LP can be labelled with a reporter (R) molecule eg fluorescein. Following SLAP the liquid phase of the reaction is discarded, the reaction vessel is rinsed and the presence of labelled product associated with the walls of the reaction vessel indicates the presence of a mutation. The specific sequence could be confirmed by hybridization of an oligonucleotide labelled with a second reporter molecule.

Figure 5:
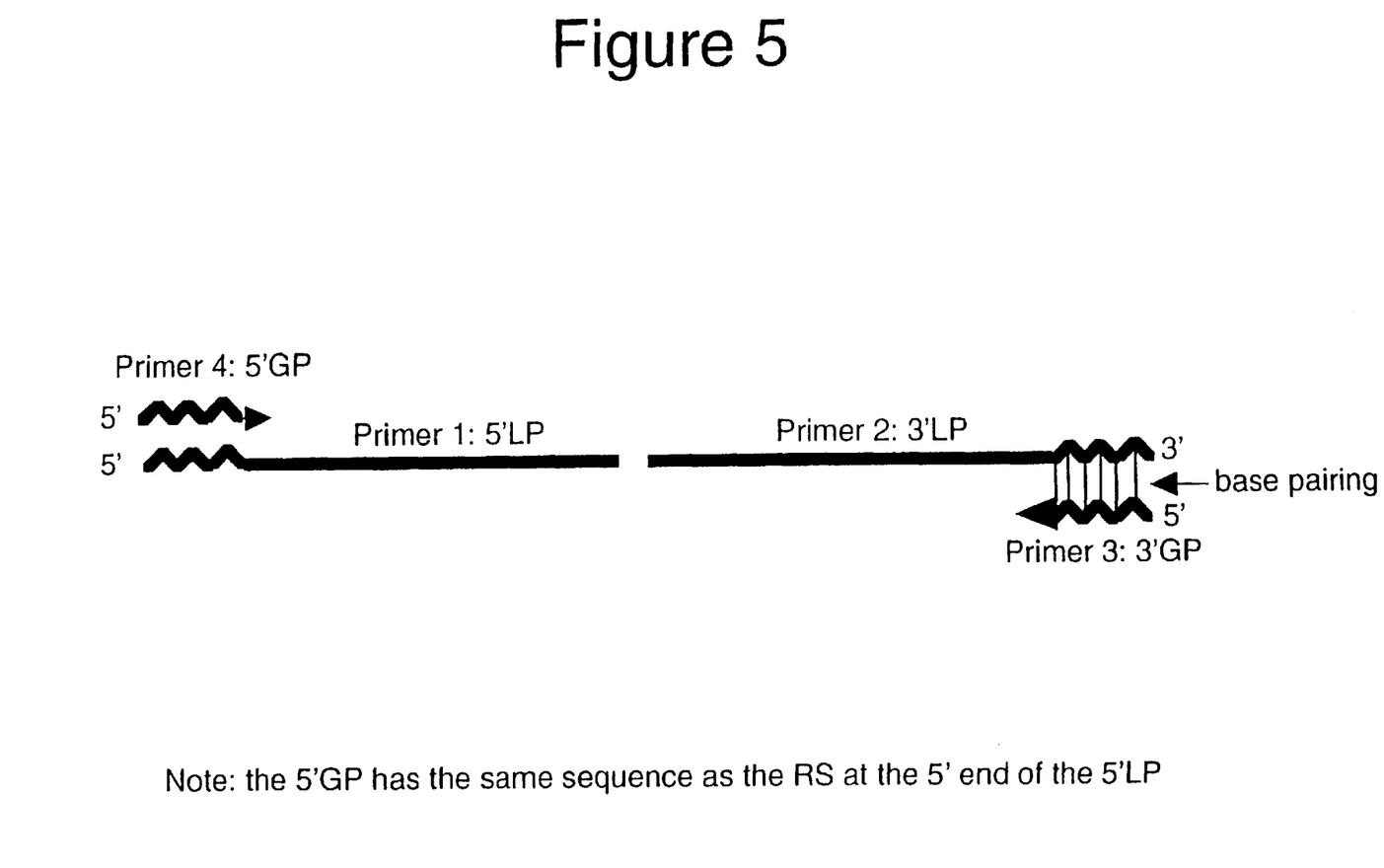
FIG. 5 SLAP—arrangement of primers in a 4 primer system.

(2) Another alternative strategy for SLAP is illustrated in FIG. 5.

Figure 6:
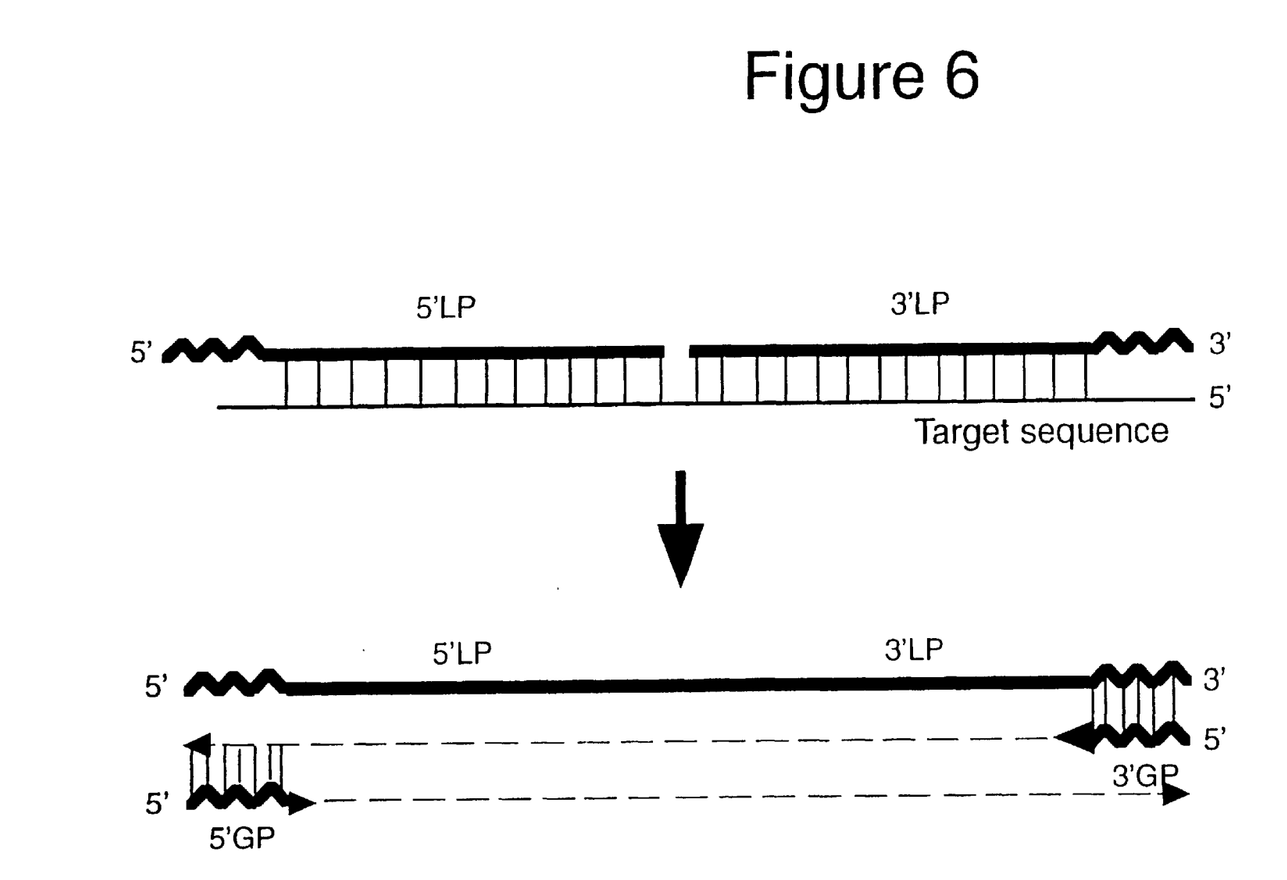
FIG. 6 Amplification with generic primers—4 primer system.

SLAP can be performed with 4 primers. In addition to the primers in the 3 primer system a fourth primer can be included. This primer is the 5' geileric primer. It has the same sequence as random sequence which is located at the 5' terminus of the 5'LP. This primer call only amplify the product produced by extension from the 3'GP (FIG. 6). Inclusion of the 5'GP primer, as well as the 3'GP, means that PCR is mediated by two generic primers and is less dependent on the efficiency of the ligation step.

EXAMPLE

Methods

A SLAP protocol was used to detect point mutations at position 1 of codon 12 in the K-ras oncogene. The human cell lines Calu I [ATCC HTB54] and T24 [ATCC HTB 4] were obtained from the American Type Culture Collection. T24 is a human bladder carcinoma cell line which is wild type at codon 12 of K-ras. Calu 1 is a lung adenocarcinoma cell line and is heterozygous at K-ras codon 12 having both wild type (GGT) and mutant (TGT) sequences (Ref 1). Genomic DNA was extracted from Calu 1 and T24 cells by an extraction protocol involving incubation of cells in a lysis buffer at high temperatures, addition of a further buffer and a cationic polymer (U.S. Pat. No. 5,582,988) which binds DNA. The polymer/DNA complex is then centrifuged to the bottom of the tube and the DNA eluted from the polymer by the addition of NaOH and incubation at high temperatures. The NaOH/DNA solution was neutralised by addition of equimolar amounts of HCl in a Tris buffer, so that the final DNA solution was in 10 mM Tris (pH ranging from 7 to 7.5) and 20 mM NaCl. DNA samples were amplified by SLAP using the LPs and GP listed in Table 1 below. The underlined sequence is homologous to the K-ras oncogene and the bold type bases in the LP's designated 5KLP3X are specific for either the wild type (X=G) or for particular mutations (X=A or T) within the K-ras oncogene. The series of priners designated 5KLP3X have hydroxyl groups are both their 5' and 3' termini, and the primer 3BKLP4 is phosphorylated at the 5' termini and biotinylated at the 3' termini The generic primer 3GP4 is complementary to the 3' region of 3BKLP4.

TABLE 1

Sequence of primers used in SLAP

| Primer | Function | Sequence |
| --- | --- | --- |
| 5KLP3G | 5'LP for G (wild type) | CAGTTAGGCCTCTCACTAGA<u>ATAAACTTGTGGTAGTTG</u> <u>GAGCTG</u> |
| 5KLP3A | 5' LP for A (mutant) | CAGTTAGGCCTCTCACTAGA<u>ATAAACTTGTGGTAGTTG</u> <u>GAGCTA</u> |
| 5KLP3T | 5' LP for T (mutant) | CAGTTAGGCCTCTCACTAGA<u>ATAAACTTGTGGTAGTTG</u> <u>GAGCTT</u> |
| 3BKLP4 | 3'LP | GGCGTAGGCAAGAGTGCCTTGACTGATCTTCGAATTCA CACG |
| 3GP4 | GP for PCR | CGTGTGAATTCGAAGATCAG |

Genomic DNA from T24, Calu 1 and Calu 1 diluted with T24 at a ratio (by weight) of 1:10, 1:$10^2$ and 1:$10^3$ was amplified by SLAP in a total volume of 100 $\mu$l. The reactions contained genomic DNA (1 ug), 5 pmole of 3GP4, 5 pmole of 3BKLP4, 5 pmole of either 5KLP3G or 5KLP3A or 5KLP3T, each dNTP (dATP, dCTP, dTTP, dGTP) at 12.5 $\mu$M, 100U of Ampligase Thermostable DNA ligase (100 units/$\mu$l, Epicentre Technologies) and 5 units of AmpiTaq$^R$ DNA polymerase, Stoffel fragment (10 units/$\mu$l; Perkin Elmer) in 1x Ampligase Reaction Buffer (25 mM KCl. 20 mM Tris-HCl (pH 8.3), 0.5 mM NAD, 10 mM MgCl$_2$ and 0.01% Triton X-100). Control reactions lacked either DNA or Ampligase Thermostable DNA ligase. The reactions were placed in a GeneAmp PCR system 2400 (Perkin Elmer), heated at 94° C. for 2 minutes and then subjected to 20 cycles of 94° C. for 20 seconds followed by 64° C. for 20 sec (with a 5 sec increase in the time spent at 64 °C. every cycle). Following this the reactions were held at 99.9° C. for 5 minutes and then subjected to a further 20 cycles of 94° C. for 20 sec followed by 64° C. for 2 minutes.

A 25 $\mu$l aliquot of each reaction was analysed without subsequent manipulation by electrophoresis on a 5% Nusieve GTG gel (FMC Bioproducts, Rockland, Md). The gel was photographed using a Stratagene Eagle Eye II video system.

The reactions were also analysed in a colorimetric assay. This assay is similar to that described in Findlay et al (2). SLAP amplicons were specifically captured by hybridization to oligonucleotide probes that were covalently attached to latex beads. The latex bead/oligonucleotide complex was applied at discrete locations in Periodontal Surecell blanks. The sequence of the capture oligonucleotides were:

SKCapD1 GCTCCAACTACCACAAGTTTATTCTAGT-GAGAG

SKCapD2 AGCTCCAACTACCACAAGTTTAT-TCTAGTGAGA

Kcap3 GCACCAGTAATATGCATATTAAAACAAG

The oligonucleotides SKCapD1 and SKCapD2 are complementary to a portion of the sequence of the 5'LP. The oligonucleotide KCap3 is complementary to a portion of the sequence exon 1 of the K-ras gene that is 3' of the 3'LP (not amplified by the SLAP protocol with the primers listed in Table 1). The probe Kcap3 thus provides a negative control for non-specific amplification and/or hybridization.

Aliquots of the three oligonucleotide latex beads (0.25% in 1.2 μl of 10 mM Tris 1 mM EDTA pH 7.4 at 25° C.) we applied on to the Surecell membrane in discrete spots with all three oligonucleotides in each Surecell well. The oligonucleotide latex beads were allowed to dry for 15 minutes. Aliquots of 25 μl of each reaction were diluted with 180 μl of 50 mM KCl, 10 mM Tris (pH 8.3 at 25° C.) and 10 mM $MgCl_2$. The diluted SLAP products were denatured at 95° C. for 6 minutes and applied to the Surecell well. The Surecells were then incubated at 50° C. for 5 minutes to allow hybridization of SLAP amplicons with the capture oligonucleotides. The wells were washed with 300 μl of 50 mM KCl, 10 mM Tris (pH 8.3 at 25° C.) and 10 mM $MgCl_2$ at 50° C. The hybridized amplicons were reacted with 150 μl of a conjugate of streptavidin bound to horseradish peroxidase (EC 1.11.1.7) and incubated at room temperature for 2 minutes. The wash step was repeated to minimise non-specific interactions. An aliquot of 200 μl of Leucodye/$H_2O_2$ was added and the Surecells were incubated at room temperature for 2 minutes. The immobilized complex served as a catalyst in the oxidative conversion of dye molecules from a colourless to a blue form. The reaction was stopped with 200 μl of 0.1% $NaN_3$. The resultant coloured spots were scored visually by comparison against a colour chart and rated from 0 (no colour) to 10 (dark blue). A further aliquot of 25 μl of each SLAP reaction was diluted with 180 μl of 50 mM KCl, 10 mM Tris (pH 8.3 at 25° C.) and 10 mM $MgCl_2$ and applied to the Surecell membrane without prior denaturation at 95° C. Detection was carried out as described above.

Results

The results of detection on the 5% Nusieve gel of SLAP analysis of Calu 1 and T24 are summarised in Table 2 below. The presence of an 88 bp fragment is diagnostic for the presence of a specific sequence at the first position of K-ras codon 12. There was no diagnostic product in reactions that did not contain DNA, or in the reactions which did not contain ligase.

A 42 bp product is present in all reactions. This small product is formed by extension of the 3GP4 which produces the complement of 3BKLP4.

TABLE 2

Results of SLAP

| 5'LP | T24 DNA | Calu 1 DNA | No DNA | 1:10 Calu 1: T24 | 1:100 Calu 1: T24 | 1:1000 Calu 1 T24 |
|---|---|---|---|---|---|---|
| 5KLP3G | 88 bp | 88 bp | | 88 bp | 88 bp | 88 bp |
|  | 42 bp | 42 bp | 42 bp | 42 bp | 42 bp | 42 bp |
| 5KLP3T |  | 88 bp |  | 88 bp | 88 bp |  |
|  | 42 bp | 42 bp | 42 bp | 42 bp | 42 bp | 42 bp |
| 5KLP3A | 42 bp | 42 bp | 42 bp |  |  |  |
| 5KLP3G (no DNA ligase) | 42 bp | 42 bp |  |  |  |  |
| 5KLP3T (no DNA ligase) | 42 bp | 42 bp |  |  |  |  |
| 5KLP3A (no DNA ligase) | 42 bp | 42 bp |  |  |  |  |

The 88 bp diagnostic product was present in the reactions which contained ligase, DNA polymerase and the 5'LP 5KLP3G with either T24 DNA, Calu 1 DNA and the dilutions of Calu 1 DNA with T24 DNA. This indicates that the wild type allele which has G at position 1 of K-ras codon 12 is present in DNA from the T24 and Calu 1 cell lines. The 88 bp diagnostic product was also present in reactions that contained ligase, DNA polymerase and the 5'LP 5KLP3T and Calu 1 DNA, or a dilution of Calu 1 DNA with T24 DNA of 1:10 and 1:100 (by weight), but not in the reactions containing T24 DNA or a dilution of Calu 1 DNA with T24 DNA of 1:1000 (by weight). This indicates the presence of a G to T mutation at the first position of codon 12 in Calt 1 DNA but not in T24 DNA. The Calu 1 cell line is therefore heterozygous containing both wild type (G) and mutant (T) bases at the first position of K-ras codon 12. The results obtained by SLAP analysis are consistent with the sequence at codon 12 in these cell lines as reported in the literature, and show that this protocol can detect 1 mutant allele in a background of at least 200 wild type alleles when analysed by standard agarose gel electrophoresis.

The results of analysis of SLAP reactions by detection on Surecells are summarised in Table 3. The detection of product with either SKCapD1 or SKCapD2 is diagnostic for the presence of a specific sequence at the first position of K-ras codon 12. There was no diagnostic product detected in reactions that did not contain DNA, or in the reactions which did not contain ligase. There was no detection with the capture oligonucleotide probe Kcap3, indicating that there was no non-specific amplification or hybridization.

TABLE 3

Results of SLAP by Surecell Analysis

| Template and 5'LP | Denatured SLAP Product | | | Non-Denatured SLAP Product | | |
|---|---|---|---|---|---|---|
|  | SKCapD1 | SKCapD2 | Kcap3 | SKCapD1 | SKCapD2 | KCap3 |
| No DNA |  |  |  |  |  |  |
| 5KLP3G | 0 | 0 | 0 | 0 | 0 | 0 |
| 5KLP3T | 0 | 0 | 0 | 0 | 0 | 0 |
| 5KLP3A | 0 | 0 | 0 | 0 | 0 | 0 |
| Calu 1 DNA |  |  |  |  |  |  |
| 5KLP3G | 6 to 7 | 6 to 7 | 0 | 4 to 5 | 4 to 5 | 0 |
| 5KLP3T | 8 | 8 | 0 | 6 to 7 | 6 to 7 | 0 |
| 5KLP3A | 0 | 0 | 0 | 0 | 0 | 0 |

TABLE 3-continued

Results of SLAP by Surecell Analysis

| Template and 5'LP | Denatured SLAP Product | | | Non-Denatured SLAP Product | | |
|---|---|---|---|---|---|---|
| | SKCapD1 | SKCapD2 | Kcap3 | SKCapD1 | SKCapD2 | KCap3 |
| T24 DNA | | | | | | |
| 3KLP3G | 7 to 8 | 7 to 8 | 0 | 3 to 4 | 3 to 4 | 0 |
| 5KLP3T | 0 | 0 | 0 | 0 | 0 | 0 |
| 5KLP3A | 0 | 0 | 0 | 0 | 0 | 0 |
| 1:10 Calu 1:T24 | | | | | | |
| 5KLP3G | 7 to 8 | 7 to 8 | 0 | 4 to 5 | 4 to 5 | 0 |
| 5KPL3T | 5 to 6 | 5 to 6 | 0 | 3 to 4 | 3 to 4 | 0 |
| 1:100 Calu 1:T24 | | | | | | |
| 5KLP3G | 7 to 8 | 7 to 8 | 0 | 4 to 5 | 4 to 5 | 0 |
| 5KLP3T | 3 to 4 | 3 to 4 | 0 | 1 | 1 | 0 |
| 1:1000 Calu 1:T24 | | | | | | |
| 5KLP3G | 7 to 8 | 7 to 8 | 0 | 3 to 4 | 3 to 4 | 0 |
| 3KLP3T | 1 | 1 | 0 | 0 | 0 | 0 |

With Surecell analysis of SLAP product that was denatured before application to the membrane, diagnostic product was detected in the reactions that contained ligase, DNA polymerase and the 5'LP 5KLP3G with either T24 DNA, Calu 1 DNA, and the dilutions of Calu 1 DNA with T24 DNA. This indicates that the wild type allele which has a G at position 1 of K-ras codon 12 is present in DNA from the T24 and Calu 1 cell lines. Diagnostic product was also detected in reactions that contained ligase, DNA polymerase and the 5'LP 5KLP3T and Calu 1 DNA, or a dilution of Calu 1 DNA with T24 DNA of 1:10, 1:100 and 1:1000 (by weight), but not in the reaction containing T24 DNA. This indicates the presence of a G to T mutation at the first position of codon 12 in Calu 1 DNA, but not in T24 DNA. The Calu 1 cell line is therefore heterozygous containing both wild type (G) and mutant (T) bases at the first position of K-ras codon 12. The results obtained in the Surecell analysis are in concordance with the previously published sequence of K-ras in these cell lines.

The same pattern of detection of diagnostic product was observed in the samples applied to the Surecell membranes with or without prior denaturation, except that the 5'LP 5KLP3T did not give detection in the reaction with Calu 1 DNA diluted 1:1000 with T24 DNA unless the SLAP product was denatured. The fact that diagnostic product was detected from SLAP product that was not denatured prior to application to the Surecell membrane indicates that single stranded product was produced by the SLAP protocol.

Overall, the results obtained by SLAP analysis are consistent with the sequence at codon 12 in these cell lines as reported in the literature, and show that this protocol can detect 1 mutant allele in a background of at least 2000 wild type alleles when analysed by Surecell detection, and 1 in at least 200 when analysis is by standard electrophoresis.

Discussion

SLAP provides a simple and rapid method which is suitable for analysis of genetic variations which are associated with disease. The activities of ligase and DNA polymerase during SLAP facilitate the selective amplification of specific sequences which vary by as little as a single base. The SLAP reaction contains all reagents, including both enzymes, at the initiation of the reaction. Reactions can be performed in a closed system which reduces the opportunity for contamination during amplification.

SLAP has advantages over other protocols which utilise PCR and ligation to mediate detection of mutant sequences. During the initial phase, mutant templates are selectively amplified by concurrent ligation and PCR. The reaction selectively amplifies mutant sequences because both the ligase and the DNA polymerase will only function provided that the primers mediating the processes are matched with the template at the position of the variant (mutant) base. During the second phase there is generation of mutant specific, single stranded product. Since at least a proportion of the ligation products present at the end of the reaction is single stranded, no denaturation or other manipulation is required prior to detection eg by capture to oligonucleotides. This reduction in the number of steps required for selective amplification makes the SLAP assay less labour intensive and more amenable to automation. Secondly, since the GP is generic, all PCR strands would be expected to be generated with approximately equivalent efficiency. The amount of product formed during SLAP is therefore less dependent on the efficiency of the initial ligation step. This increases the suitability of SLAP for the detection of multiple mutations in multiplex reactions containing several gene/mutation specific LPs. This would allow simultaneous analysis of multiple genes and/or exons in a single reaction. Alternatively, if only a single 5'LP is included in a reaction the exact nucleotide substitution can be identified. If such reactions were performed in a 96 well plate with a different 5'LP in each well, approximately 90 bases could be screened simultaneously, the specific mutation could be identified and control reactions could be included in. the analysis.

SLAP is compatible with a variety of capture and detection systems. This allows automation of the complete protocol and thus rapid analysis of large numbers of samples. Capture systems include i) complementary oligonucleotides attached to latex or magnetic beads; ii) biotinylated primers captured with avidin or streptavidin: iii) digoxigenin-labelled products captured using anti-digoxigenin antibodies; and iv) PCR primers with a GCN4 recognition tag captured on GCN4 coated plates. Detection systems include i) biotinylated PCR primers visualised with streptavidin/horseradish peroxidase; ii) direct labelling with molecules such as fluorescein-isothiocyanate or alkaline phosphatase; and iii) digoxigenin-labelled products detected using anti-digoxigenin antibodies.

It will be appreciated by persons skilled in the art that numerous variations. and/or modifications may be made to the invention as shown in the specific embodiments without departing from the spirit or scope of the invention as broadly described. The present embodiments are, therefore, to be considered in all respects as illustrative and not restrictive.

REFERENCES

1. Capon, D. J., Chen E. Y. Levinson A. D., Seeburg P. H., and Goeddel, D. V. (1983) Complete nucleotide sequences of the T24 human bladder carcinoma oncogene and its normal homologue. Nature 302; 33.

2. Findlay J. B., Atwook S. M., Bergmyer, L., Chamelli. J., Christy K., Cummins, J., Donish W., Ekeze T., Falvo J. Patterson D. Puskas J., Quenin J., Shah J., Sharkey D., Sutherland J. W. H., Sutton R. Warren W. and Wellman J. (1993) Automated closed-vessel system for in vitro diagnostics based on polymerase chain reaction. Clin. Chem. 39/9; 1927–1933.

What is claimed is:

1. A method for amplifying a specific target nucleic acid sequence, the method comprising:
   (1) forming a reaction mixture comprising:
      (i) the target sequence;
      (ii) primers comprising a first primer at least a portion of which at 3' end thereof is substantially complementary to a first segment at a first end of the target sequence, a second primer at least a portion of which at the 5' end thereof is substantially complementary to a second segment at a second end of the target sequence, the 5' end of the second primer being adjacent the 3' end of the first primer, and a third primer, the third primer being substantially complementary to a segment of the second primer at the 3' end thereof; wherein the segment of the second primer to which the third primer is substantially complementary is a random sequence;
      (iii) at least four different nucleotide bases;
      (iv) thermostable polymerase and thermostable ligase; and
   (2) thermocycling the reaction mixture.

2. A method for detecting a specific target nucleic acid sequence in a sample comprising nucleic acid, the method comprising:
   (1) forming a reaction mixture comprising:
      (i) a sample of nucleic acid suspected to include the target sequence;
      (ii) primers comprising a first primer at least a portion of which at the 3' end thereof is substantially complementary to a first segment at a first end of the target sequence, a second primer at least a portion of which at the 5' end thereof is substantially complementary to a second segment at a second end of the target sequence, the 5' end of the second primer being adjacent the 3' end of the first primer, and third primer, the third primer being substantially complementary toa segment of the second primer at the 3' end thereof; wherein the segment of the second primer to which the third primer is substantially complementary is a random sequence;
      (iii) at least four different nucleotide bases;
      (iv) thermostable polymerase and thermostable ligase;
   (2) thermocycling the reaction mixtuer; and
   (3) detecting the presence or absence of an amplification product indicative of the presence of the specific target nucleic acid sequence.

3. A method as claimed in claim 1 in which the method further comprises following the thermocycling of the reaction mixture the steps of substantially inactivating the thermostable polymerase and a subsequent second thermocycling of the reaction mixture.

4. A method as claimed in claim 1 in which the reaction mixture includes a fourth primer which has the same sequence as a segment of the first primer at the 5' end thereof.

5. A method as claimed in claim 2 in which the method further comprises following the thermocycling of the reaction mixture the steps of substantially inactivating the thermostable polymerase and a subsequent second thermocycling of the reaction mixture.

6. A method as claimed in claim 2 in which the reaction mixture includes a fourth primer which has the same sequence as a segment of the first primer at the 5' end thereof.

* * * * *